United States Patent [19]

Frechet et al.

[11] Patent Number: 5,334,310
[45] Date of Patent: Aug. 2, 1994

[54] COLUMN WITH MACROPOROUS POLYMER MEDIA

[75] Inventors: Jean M. J. Frechet; Frantisek Svec, both of Ithaca, N.Y.

[73] Assignee: Cornell Research Foundation, Inc., Ithaca, N.Y.

[21] Appl. No.: 965,181

[22] Filed: Oct. 23, 1992

Related U.S. Application Data

[63] Continuation-in-part of Ser. No. 779,929, Oct. 21, 1991, abandoned.

[51] Int. Cl.$^5$ ............................................. B01D 15/08
[52] U.S. Cl. ............................ 210/198.2; 210/502.1; 210/635; 210/656; 95/88; 96/101
[58] Field of Search ...................... 210/635, 556, 198.2, 210/502.1; 422/70; 436/161; 95/88; 96/101

[56] References Cited

U.S. PATENT DOCUMENTS

| | | | |
|---|---|---|---|
| 3,598,728 | 8/1971 | Bixler | 210/635 |
| 3,796,657 | 3/1974 | Pretorius | 210/635 |
| 3,808,125 | 4/1974 | Good | 210/198.2 |
| 3,878,092 | 4/1975 | Fuller | 210/198.2 |
| 3,954,608 | 5/1976 | Valentin | 210/635 |
| 4,340,483 | 7/1982 | Lukas | 210/198.2 |
| 4,447,328 | 5/1984 | Kamiyama | 210/635 |
| 4,486,311 | 12/1984 | Nakajima | 210/635 |
| 4,497,710 | 2/1985 | Wagu | 210/635 |
| 4,565,832 | 1/1986 | Kobasi | 210/635 |
| 4,747,956 | 5/1988 | Kiniwa | 210/690 |
| 4,889,632 | 12/1989 | Svec | 210/500.37 |
| 4,913,812 | 4/1990 | Moriguchi | 210/635 |
| 4,923,610 | 5/1990 | Svec | 210/637 |
| 4,952,349 | 8/1990 | Svec | 264/45.1 |

FOREIGN PATENT DOCUMENTS

| | | | |
|---|---|---|---|
| 231684 | 12/1987 | European Pat. Off. | 210/198.2 |
| 6803739 | 9/1969 | Netherlands | 210/198.2 |
| 1188736 | 4/1970 | United Kingdom | 210/198.2 |
| WO9007965 | 7/1990 | World Int. Prop. O. | 210/198.2 |

OTHER PUBLICATIONS

Snyder, Introduction to Modern Liquid Chromatography, John Wiley & Sons, Inc., New York, 1979, pp. 183–195, 492–494, and 203–204.

Kumakura, "Characteristic of Porous Polymer Composite Columns Prepared by Radiation Cast-Polymerization," Journal of Materials Science 24 (1989) pp. 1809–1813.

Hjerten, "High-Performance Liquid Chromatography on Continuous Polymer Beads," Journal of Chromatography 473 (1989) pp. 273–275.

*Primary Examiner*—Ernest G. Therkorn
*Attorney, Agent, or Firm*—Bruce Jacobs

[57] ABSTRACT

A continuous liquid chromatographic column containing a separation medium in the form of a macroporous polymer plug is disclosed. The column possesses numerous advantages over conventional columns which are packed with beads or particles. The plug contains both small pores less than 200 nm in diameter and large pores greater than 600 nm in diameter.

16 Claims, 6 Drawing Sheets

COLUMN WITH MACROPOROUS POLYMER MEDIA

CROSS TO RELATED APPLICATION

This application is a continuation-in-part of U.S. Ser. No. 07/779,929, filed Oct. 21, 1991, now abandoned.

BACKGROUND OF THE INVENTION

Conventional chromatography is generally carried out by the passage of a sample that is to undergo chromatographic separation through a bed of spherical beads. These beads are usually packed in a tube or column in a manner to minimize interstitial volume between the beads so as to increase the efficiency of the column. The traditional synthetic route to make spherical particles is through suspension polymerization. In this kind of polymerization the choice of monomers is limited to those which are not soluble in the dispersion phase. Thus, the technique is not applicable to all polymers. This technique is easy to carry out, but the beads that are obtained are of rather polydispersed sizes. Therefore, a tedious and repetitive size fractionation must generally be carried out to obtain uniformly sized beads for packing. As a result, the packing of a column in this fashion is time-consuming and expensive.

To improve the efficiency of columns, the use of small particles or beads is desirable since such beads generally pack more easily leaving less interstitial volume. Synthesis of small porous beads is achievable, such as by a seeded polymerization, and such beads have been used in columns to achieve higher efficiencies. The use of increasingly smaller beads has, however, caused problems, since the smaller the beads, the shorter the column that is required. Certain problems associated with a short column can be solved. The column volume of such short columns is reduced (resulting in a lower separation capacity) unless reduction in length is compensated for by an increase in diameter. The best results for a separation are usually achieved when the diameter of the pores of the beads exceeds the Stockes diameter of the macromolecule to be separated by threefold or more. As a result, the beads must be very porous and therefore they are even more difficult to pack because they have a low mechanical strength. The trend to further decrease particle size in order to increase the speed and resolution of liquid chromatography columns seems to be coming to an end due to these technical limitations.

Current good quality chromatographic packings possess porosities of about 50 to 60%. Methods to increase the pore volume are known but the more porous packings that would result would likely be so brittle that their mechanical properties would not reach the standards that are expected for HPLC. Other less conventional approaches to improve column efficiency have been tried.

For example, Bio Rad manufactures Bio-Rex ®, 0.4 mm thick flexible disks comprising styrene-divinylbenzene ion-exchange resin (90%) in a Teflon ® polymer web (10% of the overall volume) for chromatographic separation of proteins. The use of 10% Teflon, polymer, even if perfectly placed between beads, can not fully occupy the interstitial space between them, leaving some voids between particles. This will prevent the column from reaching its theoretical maximum efficiency.

PCT Publication WO 90/07965 discloses a chromatographic column plug suitable for use with gravity flow, not with pressurized flow. The plug contains cracks and channels sufficiently large to permit a hydrodynamic flow. The plug comprises a polymerized mixture of acrylic acid and methylenebisacrylamide. Hjerten et al., *J. Chromatography*, 473 (1989), 273-275, published 2 months after the filing of PCT Pub. WO 90/07965, discloses that the plugs disclosed in the PCT publication can not be used for chromatography, since they collapse when pressure is applied. In order to solve this problem, Hjerten recommends strongly compressing the plug to increase its resolution and ability to withstand pressure. Such compression would inherently produce non-uniform channels within the plug resulting in less than ideal column efficiency.

U.S. Pat. Nos. 4,889,632, 4,923,610 and 4,952,349 (Svec et al.) disclose thin layer macroporous membranes for so-called "membrane chromatography". The membranes are punched from a macroporous sheet of polymer and the cartridge in which they are used is different from and not a column. In fact, membrane chromatography is not chromatography since there are no repeated sorption-desorption steps as the separated molecule passes through the membrane.

Kumakura et al., *J. Mat. Sci.*, 24 (1989), 1809-13, disclose a porous polymer composite column. The polymer material is produced from a combination of monomers by means of a radiation casting polymerization at $-78°$ C. The resulting polymer material contains extremely large holes of 10 to 40 microns in diameter, and not submicron pores. As a result, column efficiency is far less than ideal.

Accordingly, none of these approaches completely solve the problems associated with conventional packed bed chromatography columns.

EP 0,231,684 discloses chromatography columns with cast in place porous ceramic, i.e. inorganic, plugs which merely maintain separation media in place, either directly in liquid chromatography devices or indirectly as restrictors in supercritical fluid chromatographic devices. The ceramic plug is not a separation medium.

Dutch patent application No. 6,803,739 discloses the copolymerization of a solution of ethylene glycol bismethacrylate and ethylene glycol monomethacrylate in benzene in a flexible polytetrafluoroethylene tube. After polymerization, the benzene is removed and replaced by ethylene glycol monomethyl ether. The filled column that was obtained was used for gas-liquid chromatography. The column needs to be filled with ethylene glycol monomethyl ether in order to separate compounds in a gas-liquid chromatographic operation.

Thus, it is one of the objects of the present invention to produce a separation media for use in a chromatographic column that is compact and has substantially no interstitial volume.

It is another object of the present invention to produce a chromatographic column that can be prepared easily and inexpensively.

It is a further object of the present invention to produce a polymeric, i.e. organic, separation media from a large variety of monomers so that the separation media can be tailored to suit the end use of the column.

It is a further object is the production of a continuous bed which will be a separation medium for the separation of very large entities, such as protein aggregates, micelles, or nucleic acids. Certain of these large entities cannot be separated in a conventional packed column because they undergo degradation due to the shear forces in interstitial spaces between the packed particles.

These and still further objects of the present invention will be evident from the following description of the present invention.

DISCLOSURE OF THE INVENTION

Accordingly, the present invention is directed to a continuous column, preferably a chromatographic column, containing therein at least one plug of a continuous macroporous polymer material disposed in the column across its internal cross-sectional area. The resulting column is useful as a chromatographic column and it will also find utility in various catalytic, diagnostic, and absorption processes due to its ability to pass liquids therethrough. The macroporous polymer material according to this invention has a solvent regain (ability to accommodate a non-solvating solvent within its pores) of greater than about 0.1 ml/g, preferably greater than 0.5 ml/g. The materials contain not only small pores, i.e. those below about 200 nm in diameter, but also large pores, i.e. those at least about 600 nm in diameter. The plug of macroporous media that extends across the internal cross-sectional area of the column generally has a thickness of at least about 5 mm. The thickness distinguishes the plug from a mere membrane. The plug is preferably an elongated rod-shaped material having a thickness (or length) ranging from about 5 to 200 mm. While it is currently preferred to employ a single plug, multiple plugs may also be used, especially when the multiple plugs have different compositions or structures. It is therefore possible to engineer the sorption properties within a single continuous column instead of using multiple columns in a row. Thus, the upper plug may possess suppression properties for ion chromatography of conflicting ions while the following plug performs the desired separation.

The macroporous polymer plug is produced by polymerizing a polyvinyl monomer or, more preferably, a mixture of a polyvinyl monomer and a monovinyl monomer, in the presence of an initiator and a porogen. The polymerization mixture may also contain macroporous polymeric particles. The polymerization mixture is added to the column and polymerization is initiated therein so as to form a macroporous polymer plug. The organic polymer plug is then washed with a suitable liquid to remove the porogen.

A chromatographic column containing at least one macroporous polymer plug separation media of this invention possesses advantages over the prior art packed columns. For example, the columns of the present invention are compact due to the absence of interparticular volume. This results in a very high permeability ratio and thus a very high column efficiency. The column is easy to prepare since tedious packing of beads or particles is not required. Rather, the column of the present invention is prepared using a simple polymerization process which is carried out in the presence of a porogen. Another advantage of the column of this invention is the versatility in the selection of monomer chemistry used to form the separation media. This versatility results from the flexibility of the macroporous polymer process in which a plurality of different monomers may be used.

DETAILED DESCRIPTION OF THE PREFERRED EMBODIMENTS

More particularly, the columns of the present invention comprise a substantially rigid tube which while preferably cylindrical may also be rectangular or polygonal. The tube may be made from any of the conventional materials used to form chromatographic columns including metal, glass, and rigid polymers, more preferably stainless steel. Although the tube may have a limited amount of flexibility, it must be substantially rigid so that there is substantially no change in volume of the tube during the polymerization reaction. When the tube is to be used as a liquid chromatographic column, each end of the tube is closed with a fitting for connection to a liquid chromatograph. Any conventional fitting known in the art may be used.

Within the tube is disposed at least one plug of macroporous organic polymer. The plug extends completely across the internal cross-sectional area of the tube so that the sample passing through the plug, which acts as the separation media for the column, must pass through the plug. The plug is generally greater than about 5 mm thick distinguishing it from a membrane. Its overall dimension will, of course, depend upon the size of the column. Generally, the plug will have a cross-sectional area ranging from square micrometers to square meters (limited only by the size of the tube that is available) and a thickness or length of from about 5 to 200 mm or more. One plug or a plurality of plugs may be used to extend the length in the tube that is occupied by the macroporous plug. When more than one plug is used they may be of the same or different sizes and/or compositions.

The resulting plug, in addition to containing small pores less than about 200 nm, contains very large pores. A portion of the porosity is provided by large pores having diameters greater than about 600 nm up to about 3,000 nm. Preferably the large pores are from about 800 to 2,500 nm, more preferably from about 800 to 2,000, and most preferably about 900 to 2,000 nm in diameter. The large pores represent at least about 10% of the total pore volume of the plug. When the large pores are less than about 10% of the total pore volume, the back pressure would be too high. Preferably the large pores represent at least about 20% of the total pore volume, since the more large pores the lower the back pressure to force a liquid therethrough. The large pores may even represent more than 50% of the total pore volume.

The small pores generally have sizes in the range of about 0.8 to 200 nm, more preferably about 1 to 100 nm.

The resulting plug is also sufficiently rigid such that the plug is usable as a separation medium in a liquid chromatograph at the pressures at which such devices normally operate, i.e. up to about 40 MPa (6,000 psi). The plug has a balance of appropriate macroporosity and physical strength that a liquid composition including one or more organic solvents and water can pass through a plug 150 mm thick under a pressure of less than about 30 MPa (4,500 psi) at a linear flow rate of at least about 200 cm/hr.

The process for producing the columns generally comprises (1) adding to a rigid tube sealed at both ends a deaerated polymerizable mixture containing a porogen; (2) polymerizing the mixture to form a macroporous polymer plug; and (3) washing the plug (or plugs) with a solvent so as to remove the porogen present in the macroporous polymer produced.

The polymerization mixture at a minimum contains at least one polyvinyl monomer, a free radical generating initiator, and a porogen. The mixture may also contain one or more monovinyl monomers and/or soluble polymers or insoluble macroporous polymer particles.

Suitable polyvinyl monomers include divinylbenzene, divinylnaphthalene, divinylpyridine, alkylene dimethacrylates, hydroxyalkylene dimethacrylates, hydroxyalkylene diacrylates, oligoethylene glycol dimethacrylates, oligoethylene glycol diacrylates, vinyl esters of polycarboxylic acids, divinyl ether, pentaerythritol di-, tri-, or tetramethacrylate or acrylate, trimethylopropane trimethacrylate or acrylate, alkylene bis acrylamides or methacrylamides, and mixtures of any such suitable polyvinyl monomers. The alkylene groups generally contain about 1–6 carbon atoms.

Monovinyl monomers which may be used include styrene, ring substituted styrenes wherein the substituents include chloromethyl, alkyl with up to 18 carbon atoms, hydroxyl, t-butyloxycarbonyl, halogen, nitro, amino group, protected hydroxyls or amino groups, vinylnaphthalene, acrylates, methacrylates, vinylacetate, vinylpyrolidone, and mixtures thereof. The polyvinyl monomer or polyvinyl monomer plus the monovinyl monomer are generally present in the polymerization mixture in an amount of from about 10 to 60 vol. %, and more preferably in an amount of from about 20 to 40 vol. %.

The porogen that is used may be selected from a variety of different types of materials. For example, suitable liquid porogens include aliphatic hydrocarbons, aromatic hydrocarbons, esters, alcohols, ketones, ethers, solutions of soluble polymers, and mixtures thereof. The porogen is generally present in the polymerization mixture in an amount of from about 40 to 90 vol %, more preferably from about 60 to 80 vol %.

Soluble polymers and insoluble polymer particles may be employed in combination with the monomers. These polymers are added to the polymerization mixture prior to polymerization. The soluble polymers are dissolved out of the plug after its formation by passing a solvent through the plug. The soluble polymers serve as a polymeric porogen to increase the porosity of the final plug. Suitable soluble polymers used herein include non-crosslinked polymers or copolymers of such monomers as styrene or ring substituted styrene, acrylates, methacrylates, dienes, vinylchloride, and vinylacetate. The insoluble polymer particles are used to reduce the volume shrinkage during the polymerization. The lesser the volume of the monomers in the polymerization mixture the smaller the contraction of volume upon polymerization. Suitable insoluble polymer particles used herein include macroporous polymer particles which are crosslinked copolymers of the same monomers. It is, however, presently preferred due to compatibility to employ insoluble polymer particles which are formed from the same monomers used to form the polymerization mixture with which they are to be combined. The polymer particles initially have a diameter of from about 1 to 1,000 micrometers. It is not necessary that the mixture of polymer particles have the same particle size. In fact, it is more economical and, therefore presently preferred, to use irregularly sized polymer particles. While not necessary, the polymer particles may be soaked with a liquid immiscible with the polymerization mixture which can contain an inhibitor which inhibits free radical polymerization. This is done in order to prevent polymerization in the inside of the macroporous particles which would cause filling of the pores and would effectively remove them from the separation process. The rod would then contain nonporous pools unable to contribute to the separation process. Suitable inhibitors include cupric chloride and sodium nitrite. The inhibitor is generally present in an amount of from about 0.001 to 1 wt %, and more preferably in an amount of from about 0.1 to 1 wt %, based on the total weight of particles.

The polymer particles are preferably degassed prior to use in the polymerization mixture. This may be accomplished by any of the conventional means known in the art. It, however, is presently preferred to soak the particles in water, optionally containing a polymerization inhibitor, and remove the air from the pores by keeping the water-polymer particle mixture under the vacuum of a water pump for a suitable period of time such as about 5 to 20 minutes. Excess water may then be removed by filtering. The soluble polymers are generally present in an amount of from about 5 to 40% by volume of the polymerization mixture and the insoluble polymer particles in an amount of from about 5 to 50% by volume.

Conventional free-radical generating polymerization initiators may be employed to initiate polymerization. Examples of suitable initiators include peroxides such as OO-t-amyl-O-(2ethylhexyl)monoperoxycarbonate, dipropylperoxydicarbonate, and benzoyl peroxide, as well as azo compounds such as azobisisobutyronitrile, 2,2'-azobis(2-amidinopropane)dihydrochloride, and 2,2'-azobis(isobutyramide)dihydrate. It has been found that the choice of initiator may be used as a means to control the pore distribution in a plug. The initiator is generally present in the polymerization mixture in an amount of from about 0.2 to 5% by weight of the monomers.

Prior to the addition of the polymerization mixture to the tube, the mixture is deaerated by conventional means such as bubbling an inert gas such as nitrogen into the mixture for a sufficient period of time to remove oxygen present in the mixture. Once the polymerization mixture is prepared and deaerated, it is added to a tube sealed at both ends by suitable fittings. All of the polymerization mixture may be added and then polymerized to form a single plug. Alternatively, the polymerization mixture may be added in parts with polymerization being performed after each addition and before the addition of the next part. If the same monomer mixture is used in the successive additions, a single plug column is obtained. If 2 or more different polymerization mixtures are used successively, the process results in 2 or more different plugs. Presently preferred is the single plug column as it affords a better match to the current conventional packed column. The multiple plug technique is difficult to apply with conventional instruments and will be best used with a new chromatographic mode that takes advantage of the special combination of different separation media in one single column. Then the tube is sealed in preparation for polymerization.

Once the mixture is in the tube, polymerization is carried out in a conventional manner, generally at a temperature of from about 50° to 90° C. for a period of from about 6 to 24 hours, depending on the initiator and monomers used. The polymerization is preferably carried out in an inert atmosphere such as nitrogen or argon. While heating may be supplied by any means known in the art, it is presently preferred to immerse the sealed tube containing the polymerization mixture into a heated bath. Shrinkage that occurs during polymerization influences the overall pore structure but contact with the walls of the rigid tube is maintained.

After polymerization is complete, the solid macroporous polymer plug is washed to remove any porogenic solvent and with a suitable solvent to dissolve any soluble polymer present. Suitable washing solvents include methanol, ethanol, benzene, toluene, acetone, tetrahydrofuran, and dioxan. This washing process may be done in stages; for example, by washing with a solvent, then with water and then a solvent again, or by continuous washing with a solvent. The washing step is preferably carried out by pumping the solvent through the tube filled with the macroporous polymer.

In certain situations, especially those wherein it is advantageous to the subsequent use of the column to add certain functional groups to the macroporous polymer, the polymer may be treated with a suitable material to add specific functional groups. For example, wherein the macroporous polymer comprises polymerized glycidyl methacrylate, the polymer may be reacted with an amine such as diethylamine to give N,N-diethylamino-2-hydroxypropyl (DEAHP) groups or with triethylamine hydrochloride to give quaternary trimethylamino (Q) groups, the epoxy groups groups of the polymer may be also first hydrolyzed and subsequently reacted with chloroacetic acid to give carboxymethyl (CM) groups or with oleum-1,4-dioxan complex to give sulfonic (SP) groups. These groups are essential for protein separation using ion-exchange chromatography. The macroporous polymer may be provided with hydrophobic groups by the reaction with alcoholates, e.g. potassium butylate, octylate, and hexadecylate. This set of groups is essential for separation in hydrophobic interaction and reversed-phase modes. The polymer may also react with affinants specific for a single compound or small group of compounds and then it may be used in affinity chromatography. Suitable affinants are antibodies, antigens, dyes, sugars, lectins, proteins, and nucleic acids. In a similar manner, polymers based on other monomers may also be modified and used in all of the modes of chromatography. Thereafter, the plug may be washed with a suitable solvent either stagewise or in a one-step procedure.

Still another alternative relating to the washing step involves removing the polymerized plug from the tube, washing it with a suitable solvent, and then returning it to the tube. The returned polymer may be left as is or it may be swelled to occupy more space in the tube by washing the polymer with a swelling solvent such as tetrahydrofuran, 1,4-dioxan, toluene, or halogenated hydrocarbons.

After the washing step, the tube containing the macroporous polymer is ready for use. It may be used as a continuous chromatographic column as well as for catalytic, diagnostic, or absorption processes in accordance with conventional techniques known in the art. For example, when the tube is used as a chromatographic column to separate a sample into its components water or a buffer solution can serve as a carrier for the sample. The solution containing the sample is passed through the plug in the tube by pumping. The separation proceeds by changing the properties of the eluent, e.g. pH, ionic strength, content of an organic solvent, and the like. The gradient of composition may have any shape such as linear, step-like, or logarithmic. Detection of the separated sample may then be accomplished by means known in the art, either in the column itself, using staining techniques, or downstream of the plug, or outside the tube as the components elute individually from the column. The macroporous polymer separation media according to this invention is effective for separation of materials having molecular weights ranging from about hundreds to millions. Any separation which can be done with a packed column can be performed with the column of this invention.

The present invention will now described with reference to the following non-limiting examples in which all parts and percents are by weight unless otherwise noted.

EXAMPLE I

One end of a stainless steel tube (4.6 mm inner diameter, 50 mm length) provided on both ends with fittings for attachment to a liquid chromatograph was closed with a steel nut stopper, the tube was purged with nitrogen and its other end was closed with a silicon rubber septum. A polymerization mixture was prepared by mixing 4.8 g glycidyl methacrylate, 3.2 g ethylene dimethacrylate, 10.8 g cyclohexanol, 1.2 g dodecanol, and 0.08 g azobisisobutyronitrile. The mixture was bubbled with nitrogen for 20 minutes to remove any oxygen present. 0.1 ml of the mixture was injected through the septum into the tube, and polymerization was started by heating in an thermostated oil bath at 70° C. After 7 hours the tube was removed from the bath, cooled freely to room temperature, and the septum was removed. At this point the column contained a solid macroporous polymer plug 5 mm in length. After washing the polymer with methanol, both ends of the tube were closed with chromatographic nuts and the column attached to a HPLC chromatograph. First, methanol was pumped through the column at different flow rates. The back pressure was 0.4 MPa at a flow rate 0.5 ml/min, 0.8 MPa at 1 ml/min and 1.6 MPa at 2 ml/min. The solvent was then changed to tetrahydrofuran and the back pressure was 0.2 MPa at 0.2 ml/min and 19 MPa at 2 ml/min. The dependence of back pressure on flow rate was found to be linear.

After the measurements the column was opened at the bottom and the porous polymer rod was removed using solvent pressure.

EXAMPLE II

A procedure the same as that of Example I was used with the exception that 0.15 ml stock solution of the polymerization was used. The plug after removal from the tube was 9 mm long.

The plug was placed in a 50 ml round bottomed flask and 5 ml diethylamine was added. The content was refluxed for 3 hours. The epoxy groups of polymerized glycidyl methacrylate units were reacted with the amine to give N,N-diethylamino-2-hydroxypropyl groups (DEAHP) which are essential for protein separation using ion-exchange chromatography. After the reaction was finished, the rod was washed with methanol, water, methanol again, and dried. The content of the DEAHP groups was found to be 1.59 mmol/g.

The dry plug was put back to the tube of the column, immersed in water for 2 hours, the ends sealed with fittings and one end joined to the pump of a HPLC chromatograph while the other remained not connected to the detector. In this configuration the back pressure was measured. At a flow rate of 1 ml/min the back pressure was 0.5 MPa, at 3 ml/min it was 1.3 MPa, and at 5 ml/min it was 2.2 MPa. After connecting to the UV detector the back pressure increased to 0.4 MPa at a flow rate of 0.5 ml/min.

The column was washed under chromatographic conditions using a 0.02 mol/l TRIS-HCl buffer solution, pH =7.3 (buffer A) at a flow rate of 0.5 ml/min until the base line did not drift any more (20 minutes). A solution containing 0.2 lg of cytochrome C, lysozyme, myoglobin, and ovalbumin was injected through a loop and left to absorb on the continuous bed of the polymer. There was no sign of any leaking even after 20 minutes of pumping the buffer solution through the column. The absorption was total. Then a gradient elution was started. The eluent was changed from buffer A linearly to a buffer solution B (1 mol/l sodium chloride in buffer A) within a 10 min. period. Despite the fact that the chromatographic conditions far from ideal were used for this preliminary test, a separation of all four proteins was observed. The retention times of the proteins were 7.4, 7.7, 7.9, and 8.1 minutes.

EXAMPLE III

Into the same tube as used in Example I was injected 0.3 ml of a stock mixture consisting of 3 ml styrene, 1.2 ml divinylbenzene (85% of DVB), 6 ml benzylalcohol, and 0.05 g benzoylperoxide. After degassing, the tube was closed and polymerization proceeded at 70° C. for 24 hours. Using a steel plunger an 18 mm long porous polymer plug was pushed out of the tube and washed for 4 days in several portions of methanol. After the washing the plug still fit in the original tube. When the solvent was changed to tetrahydrofuran, it swelled the plug. After about 20 minutes, the diameter of the plug exceeded the diameter of the tube. In order to shrink the plug to its original size, methanol was used for subsequent exchange of the solvent. The plug was then returned to the column and methanol was again exchanged back to tetrahydrofuran. The swelling in the column was monitored as a change of back pressure which increased from 0.3 MPa at the beginning when the rest of the tube was still filled with methanol to more than 10 MPa after exchanging some of the solvent. At that point the measurement was terminated to prevent any possible damage of the equipment.

EXAMPLE IV

A mixture of the monomers described in the Example I was degassed by bubbling nitrogen for 10 minutes. Macroporous poly[glycidyl methacrylate-co-ethylene dimethacrylate] beads were soaked with distilled water and the air was removed from their pores by keeping the water-polymer mixture under the vacuum of a water pump for 10 minutes. The beads were then filtered to remove excess water. About 1 ml of the beads were then filled in a glass vial with a flat bottom continuously purged with nitrogen and 0.5 ml of the degassed polymerization mixture was added, the dispersion was stirred with a glass rod, and the vial was sealed. The polymerization proceeded at 70° C. for 6 hours. After the polymerization was finished the content of the vial seemed to be homogeneous. Due to the reaction of the epoxy groups of the glycidyl methacrylate with the silanol groups of the glass surface it was impossible to remove the block from the vial without damage of the vial. Even then, separations of the glass from the block surface was very tedious. The block does not tend to split in small pieces or to separate fragments of the original beads and the connecting copolymer.

EXAMPLE V

A stainless steel column (8 mm inner diameter and 50 mm length) was sealed on one end, purged with argon and its other end closed with a silicon rubber septum. A polymerization mixture was prepared by mixing 36 ml glycidyl methacrylate, 24 ml ethylene dimethacrylate, 72 ml cyclohexanol, 18 ml dodecanol, and 0.6 g azobisisobutyronitrile. The mixture was sonicated for 15 minutes under water pump vacuum and then bubbled with nitrogen for another 15 minutes to remove dissolved gases. The tube of the column was completely filled with the polymerization mixture and the tube closed. The polymerization proceeded in a water bath at 70° C. for 8 hours. After the polymerization was completed, the column was removed from the bath and left to cool to the ambient temperature. In order to wash the rod, which was 50 mm in length, the stopper on both ends of the column was changed to chromatographic fittings and the column was attached to the HPLC chromatograph. First, methanol was pumped throught the column at different flow rates to wash the rod and to test the flow through the column at the same time. The back pressure was 0.8 MPa at a flow rate 0.5 ml.min., 1.9 MPa at 1 ml.min, 4 MPa at 2 ml/min, and 13 MPa at 5 ml/min. The back pressure did not change during the entire washing procedure. The total amount of the methanol pumped through the column was 200 ml.

The column was removed from the chromatograph and 1 ml diethylamine was injected through the inlet of the column. The inlet and outlet of the column were stopped with delrin plugs and the column was placed in a water bath thermostated to 60° C. for 3 hours. The unreacted amine was then washed out with methanol after attaching the column to the HPLC chromatograph. During the modification process the plug swells and the swollen polymer partly occupies the pores. This translates into a high back pressure at the beginning of the washing procedure. The back pressure was 32 MPa at a flow rate of 2 ml/min. and 15 MPa at 1 ml/min. After 50 minutes of washing with methanol, a 1:1 mixture of water-methanol was used. The back pressure increased to 20 MPa at a flow rate of 0.5 ml/min. After another hour the methanol-water mixture was changed to distilled water. The back pressure decreased to 6.6 MPa at a flow rate 0.5 ml/min and to 12.7 MPa at 1 ml/min. Finally, the column was washed with a 0.02 tool/1 TRIS-HCl buffer solution (pH 7.6) (buffer A).

At a flow rate of 0.5 ml/min the back pressure was 5.7 MPa.

Figure 1:
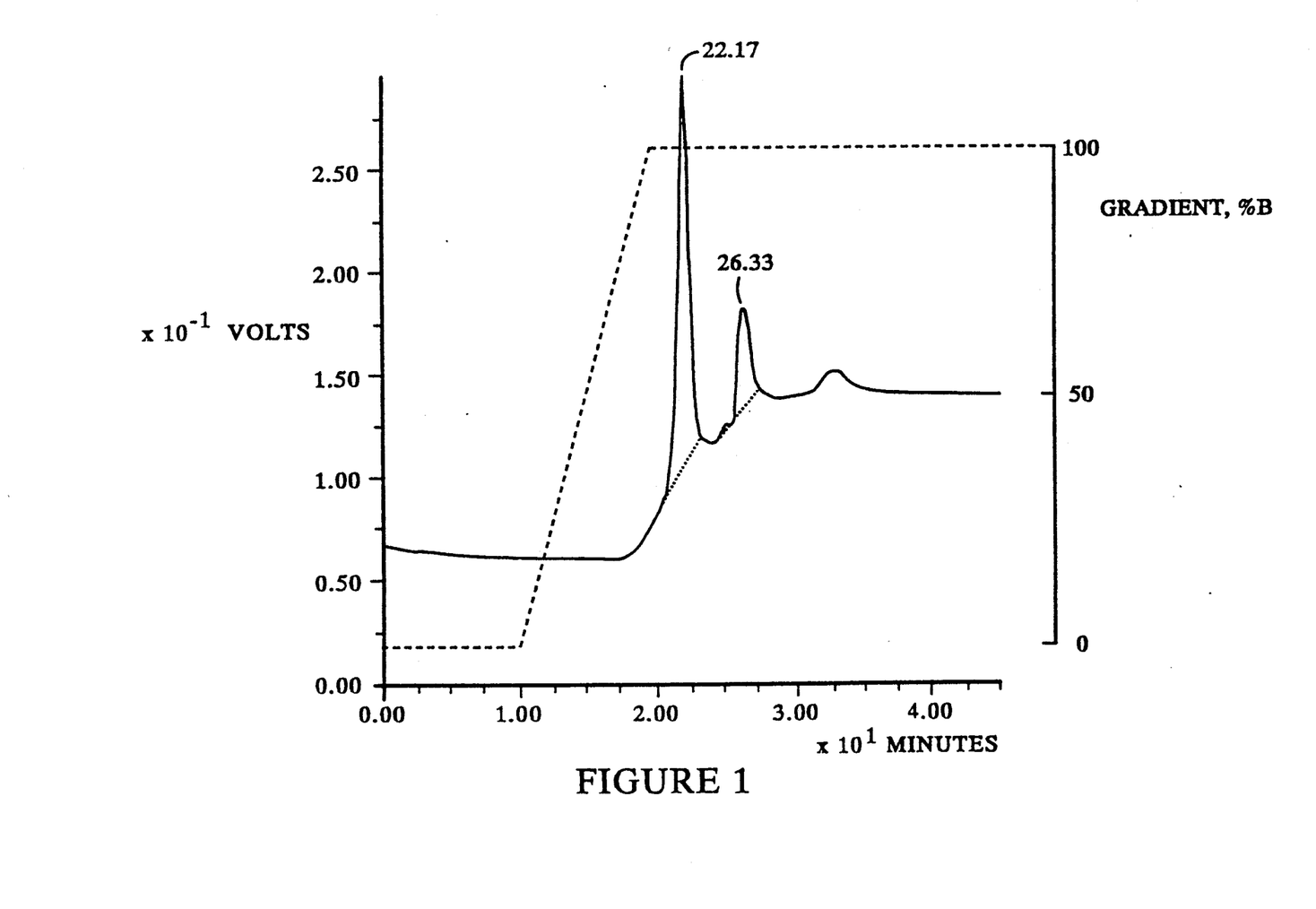
FIG. 1 is the ion-exchange chromatogram of chicken egg albumin on the continuous column of Example V.
Figure 2:
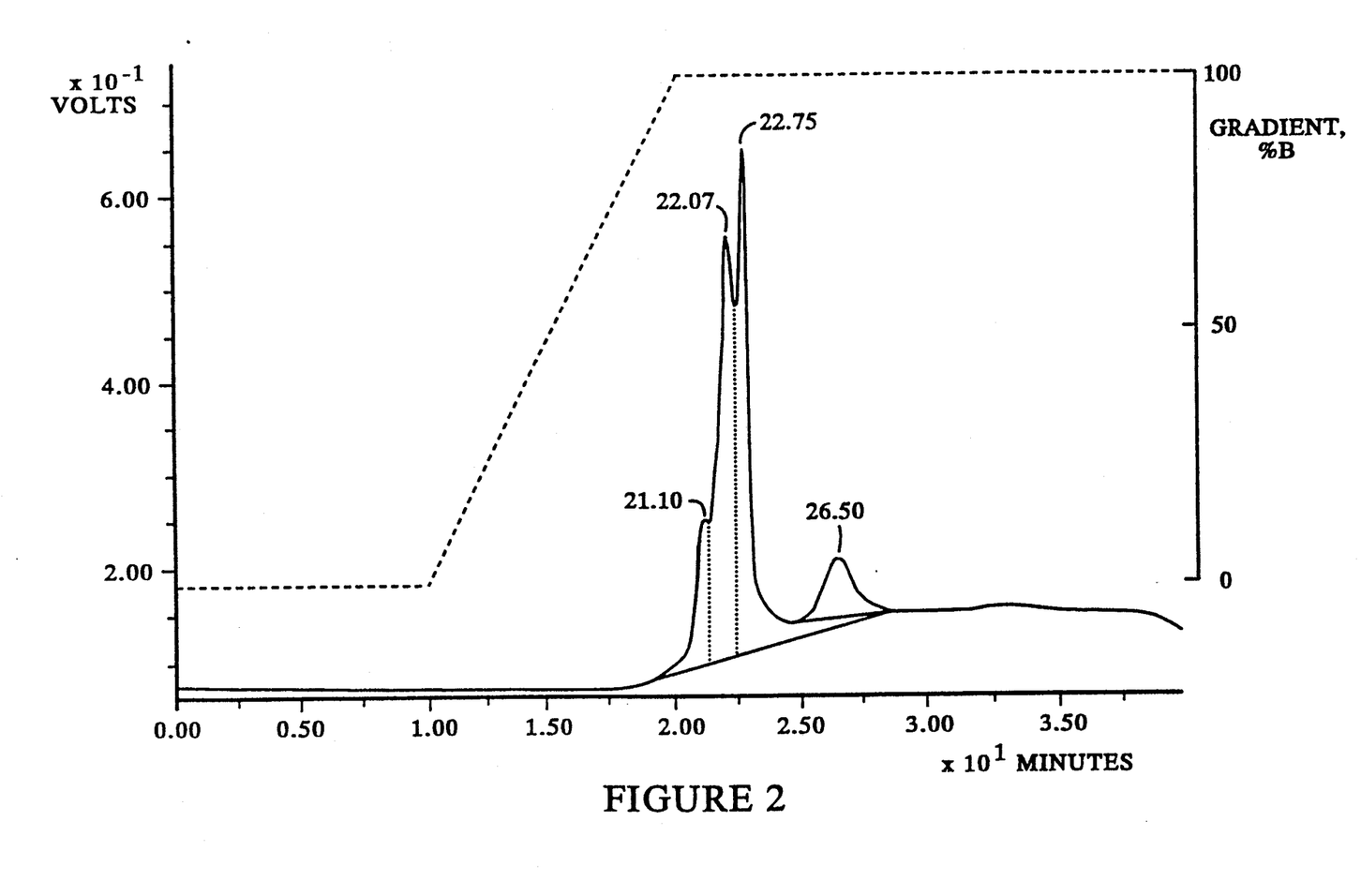
FIG. 2 is the ion-exchange chromatogram of chicken egg white protein on the continuous column of Example V.
Figure 3:
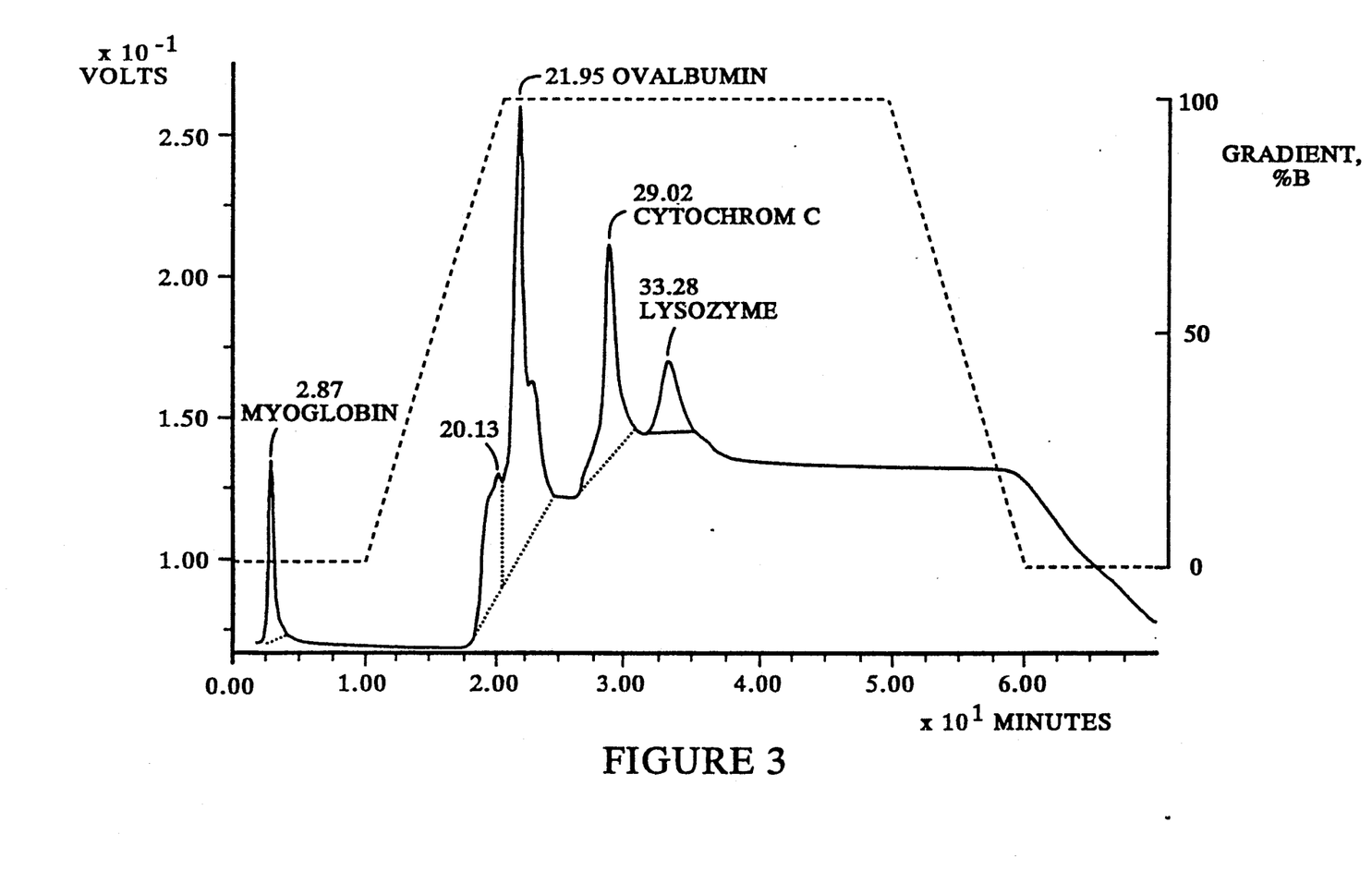
FIG. 3 is the ion-exchange chromatogram of model protein mixture on the continuous column of Example V.

Solutions (2 ll) of chicken egg albumin (8 mg/ml), chicken egg white protein (16 mg/ml), and model protein mixture (16 mg/ml) were injected through a loop and left to adsorb on the continuous macroporous polymer plug in the flow of buffer A for 10 minutes. A gradient of concentration of buffer B (1 mol/1 NACl in buffer A) was used for elution of the proteins at a flow rate 0.5 ml/min. The respective chromatograms shown in FIGS. 1-3 are for albumin (FIG. 1), egg white protein (FIG. 2) and model protein (FIG. 3) respectively. They were detected at wave length 218 nm. As is not unusual for gradient chromatography, the baseline of FIGS. 1-3 is not flat due to the gradient of solvent composition used. The solid lines in the figures are the chromatograms, and the dashed lines were added to show the changes of solvent compositions.

EXAMPLE VI

A stainless steel tube 8 mm in diameter and 50 mm long was closed on one end with a silicon rubber septum and on the other with a solid silicon rubber plug. A polymerization mixture was prepared by mixing 3 ml styrene, 2 ml divinylbenzene, 7.5 ml dodecanol, and 0.5 g azobisisobutyronitrile. The mixture was deaerated by purging nitrogen for 15 min. The mixture was injected through the septum into the steel tube and polymerization was started by heating of the tube in a thermostated air bath at 70° C. After 20 hours the tube was removed from the hot air and slowly cooled to ambient temperature. The stoppers at both ends of the column were removed and replaced with standard chromatographic column fittings. The column was attached to a chromatograph and washed with methanol at a flow rate of 0.1 ml/min for 1 hour and at a flow rate of 1 ml/min for 30 min. The back pressure during the second washing procedure was constantly 0.2 MPa.

Figure 4:
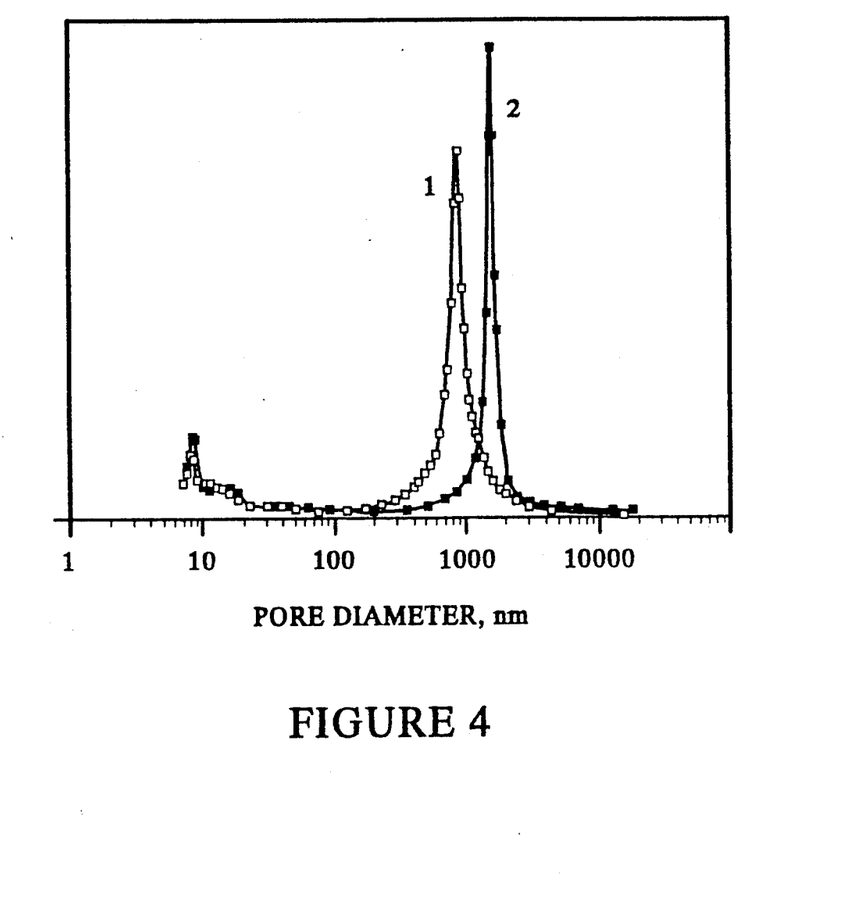
FIG. 4 is the pore size distribution curve of the plug produced in Example VI.

The column was opened at the outlet end and the polymerized rod pressed out of the column with methanol at a flow rate of 20 ml/min. The rod was dried at room temperature, crushed into smaller pieces, and evaluated for pore size distribution of the polymer using mercury porosimetry. The distribution curve is shown in FIG. 4 and it clearly documents the presence of both small pores less than 200 nm and large pores of 1,000 nm.

EXAMPLE VII

Figure 5:
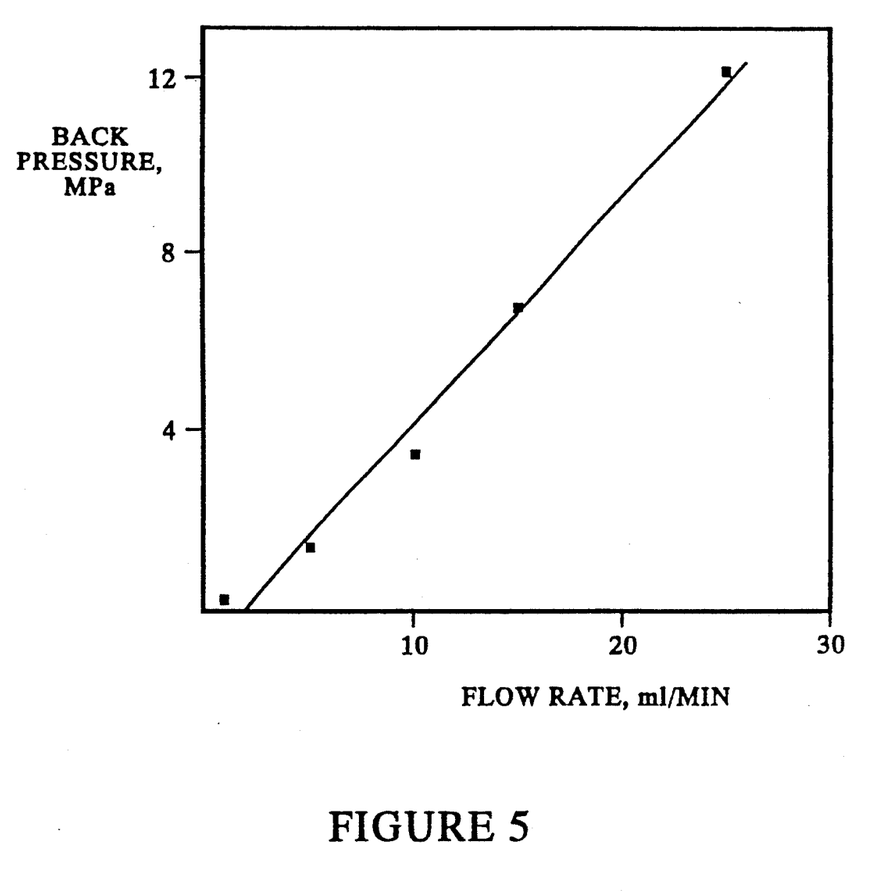
FIG. 5 is a curve showing the relationship between back pressure and flow rate through the plug of Example VII.

A column was prepared in accordance with the procedure of Example VI except that after the washing procedures with methanol were complete, the outlet fitting of the column was connected to a UV detector. The column was equilibrated 2 hours with acetonitrile-water 1:1 mixture at a flow rate of 1 ml/min. Then the equilibration was increased in several consecutive steps up to a flow rate of 25 ml/min and the back pressure recorded. The results are shown in FIG. 5 in which the linear dependence of the back pressure on the flow rate is evident. This result confirms that the continuous rod column is useful at very high flow rates while still in the range of reasonable back pressures for use in chromatography, i.e. below about 40 MPa (6,000 psi).

Figure 6:
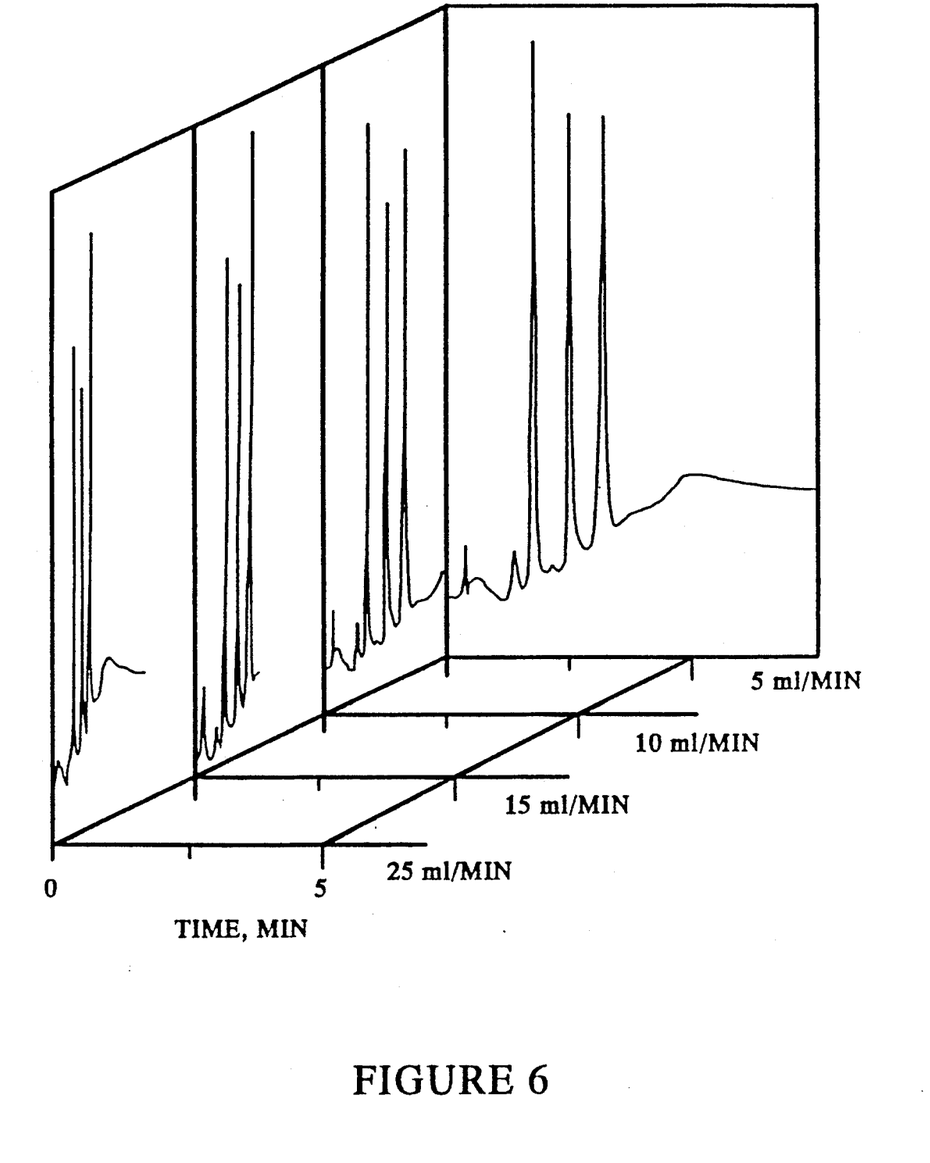
FIG. 6 is the gradient elution chromatogram of cytochome C, myoglobine, and chicken egg albumin, of the plug of Example VII.

A solution of cytochome C, myoglobine, and chicken egg albumin was injected into the column and a gradient elution chromatography started. A linear gradient from 20% acetonitrile in water to 60% acetonitrile in water was used. The time allowed for changing the acetonitrile concentration from the starting to the final mixture (the gradient time) was 4 minutes at a flow rate of 5 ml/min, 2 minutes at 10 ml/min, 1.3 minutes at 15 ml/min, and 0.8 minutes at 25 ml/min. The chromatograms are shown in FIG. 6.

COMPARATIVE EXAMPLE A

The procedure of Example 1 is repeated except that the polymerization mixture is replaced by the formulation of Dutch patent application No. 6,803,739, example II, the tube is of flexible polytetrafluoroethylene, and the polymerization temperature is 60° C. When the resulting tube and with its polymer plug is connected to a conventional chromatograph, essentially no flow of tetrahydrofuran through the plug is observed at pressures as high as 40 MPa (6,000 psi). When the plug is evaluated for pore size distribution as in Example 6 by cutting the tube apart to remove the plug, no pores larger than about 200 nm are found.

What is claimed is:

1. A continuous liquid chromatographic column comprising a rigid tube and at least one continuous plug of a macroporous organic polymer disposed within the column and extending across the cross-sectional area of the column, wherein the plug contains small pores having diameters less than about 200 nm and large pores having diameters greater than about 600 nm.

2. The column of claim 1, wherein the large pores are about 800 to about 2,500 nm in diameter.

3. The column of claim 1, wherein the large pores are about 900 to about 2,000 nm in diameter.

4. The column of claim 1, wherein the large pores provide at least about 10% of the pore volume of the plug.

5. The column of claim 1, wherein the macroporous polymer plug has a porosity of from about 30 to 90%.

6. The column of claim 1, wherein the tube contains two or more different plugs of macroporous polymer.

7. The column of claim 1, wherein the macroporous polymer comprises a polymer of a polyvinyl monomer.

8. The column of claim 7, wherein the polyvinyl monomer is selected from the group consisting of divinylbenzene, divinylnaphthalene, divinylpyridine, alkylene dimethacrylates, alkylene diacrylates, hydroxyalkylene dimethacrylates, hydroxyalkylene diacrylates, oligoethylene glycol dimethacrylates, oligoethylene glycol diacrylates, vinylesters of polycarboxylic acids, divinylether, pentaerythritol di-, tri-, or tetramethacrylate or acrylate, trimethylolpropane trimethacrylate or acrylate, alkylene bis acrylamides or methacrylamides, and mixtures thereof.

9. The column of claim 1, wherein the macroporous polymer comprises a copolymer of a polyvinyl monomer and a monovinyl monomer.

10. The column of claim 9, wherein the monovinyl monomer is selected from the group consisting of styrene, ring substituted styrenes, vinylnaphthalene, acrylates, methacrylates, vinylacetate, vinylpyrrolidone, and mixtures thereof.

11. A column comprising a rigid tube and at least one continuous plug of a macroporous organic polymer disposed within the column and extending across the cross-sectional area of the column, wherein the plug contains small pores having diameters less than about 200 nm and large pores having diameters greater than about 600 nm and wherein said column is capable of passing a liquid selected from an organic solvent and water therethrough at a linear flow rate of at least about 200 cm/hr and at a pressure of less than about 30 MPa (4,500 psi).

12. The column of claim 11, wherein the large pores provide at least about 10% of the pore volume of the plug.

13. The column of claim 11, wherein the macroporous polymer comprises a polymer of a polyvinyl monomer.

14. The column of claim 11, wherein the macroporous polymer comprises a copolymer of a polyvinyl monomer and a monovinyl monomer.

15. The column of claim 11, wherein the large pores are about about 800 to about 2,500 nm in diameter.

16. The column of claim 11, wherein the large pores are about 900 to about 2,000 nm in diameter.

* * * * *